US009457147B2

(12) United States Patent
Green

(10) Patent No.: US 9,457,147 B2
(45) Date of Patent: Oct. 4, 2016

(54) METHOD AND APPARATUS FOR ASSISTING PATIENTS IN SELF-ADMINISTRATION OF MEDICATION

(75) Inventor: Reza Green, Highland Park, NJ (US)

(73) Assignee: Novo Nordisk A/S, Bagsvaerd (DK)

(*) Notice: Subject to any disclaimer, the term of this patent is extended or adjusted under 35 U.S.C. 154(b) by 555 days.

(21) Appl. No.: 11/917,035

(22) PCT Filed: Jun. 15, 2006

(86) PCT No.: PCT/EP2006/063255
§ 371 (c)(1),
(2), (4) Date: Jul. 14, 2008

(87) PCT Pub. No.: WO2006/134153
PCT Pub. Date: Dec. 21, 2006

(65) Prior Publication Data
US 2009/0131875 A1 May 21, 2009

Related U.S. Application Data

(60) Provisional application No. 60/691,167, filed on Jun. 16, 2005.

(30) Foreign Application Priority Data

Sep. 30, 2005 (EP) .................... 05109085

(51) Int. Cl.
A61M 5/178 (2006.01)
(52) U.S. Cl.
CPC .......... A61M 5/178 (2013.01); A61M 2205/50 (2013.01); A61M 2205/581 (2013.01); A61M 2205/582 (2013.01); A61M 2205/583 (2013.01)

(58) Field of Classification Search
CPC .................. A61M 2205/581; A61M 2205/18; A61M 2205/59; A61M 2205/80; A61M 16/0061; A61M 5/178; A61M 2205/50; A61M 2205/582; A61M 2205/583
USPC ............. 604/31, 65, 67, 131, 181, 186, 187, 604/189, 207, 218, 246
See application file for complete search history.

(56) References Cited

U.S. PATENT DOCUMENTS 4,950,246 A * 8/1990 Muller .......................... 604/154
6,165,155 A  12/2000 Jacobsen et al.
(Continued)

FOREIGN PATENT DOCUMENTS

EP    0 293 958 A1    12/1988
EP    0319272 A2       6/1989
(Continued)

OTHER PUBLICATIONS

Search Report issued in connection with counterpart European Application No. 05109085.0, mailed Mar. 3, 2006.
International Search Report and Written Opinion issued in connection with counterpart International Application No. PCT/EP2006/063255, mailed Sep. 28, 2006.
International Preliminary Examination Report issued in connection with counterpart PCT Application No. PCT/EP2006/063255, mailed Jan. 3, 2008.

Primary Examiner — Kevin C Sirmons
Assistant Examiner — Lauren M Peng
(74) Attorney, Agent, or Firm — Wesley Nicolas

(57) ABSTRACT

The present invention relates to a manual injection pen (1) suitable for injecting a liquid medication via a non-electrical drive mechanism (33). The injection pen (1) is provided with a plurality of sensors (50,70,200) that senses when a user is taking a specific action with the device. Further the injection pen (1) is provided with a sound generator (10) that generates a particular sound corresponding to the specific action taken by the user. In this way a characteristic sound signal can be provided for each specific action.

6 Claims, 1 Drawing Sheet

(56) References Cited

U.S. PATENT DOCUMENTS

| | | | |
|---|---|---|---|
| 6,171,276 B1* | 1/2001 | Lippe | A61M 5/20 128/DIG. 1 |
| 6,485,465 B2* | 11/2002 | Moberg | A61M 5/1456 417/18 |
| 6,620,133 B1* | 9/2003 | Steck | 604/131 |
| 6,786,885 B2* | 9/2004 | Hochman | A61M 5/1456 128/DIG. 12 |
| 2003/0130853 A1* | 7/2003 | Maire | 704/275 |
| 2004/0073168 A1* | 4/2004 | Takatsuka et al. | 604/131 |
| 2004/0210199 A1 | 10/2004 | Atterbury et al. | |
| 2005/0182358 A1* | 8/2005 | Veit et al. | 604/93.01 |
| 2006/0037158 A1* | 2/2006 | Foley et al. | 15/105 |

FOREIGN PATENT DOCUMENTS

| | | |
|---|---|---|
| EP | 1170024 B1 | 1/2002 |
| EP | 1518575 A1 | 3/2005 |
| JP | 2001-517496 A | 10/2001 |
| JP | 2005-507714 A | 3/2005 |
| WO | WO 02/32287 A3 | 4/2002 |
| WO | 2005/046559 A2 | 5/2005 |

* cited by examiner

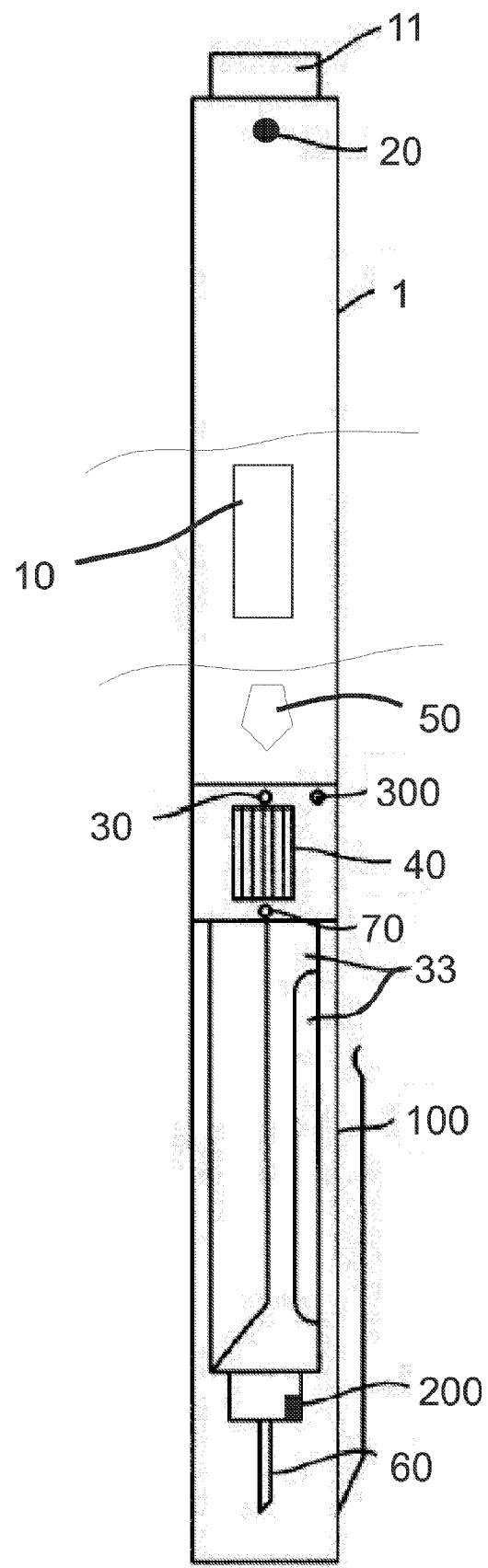

METHOD AND APPARATUS FOR ASSISTING PATIENTS IN SELF-ADMINISTRATION OF MEDICATION

CROSS-REFERENCE TO RELATED APPLICATIONS

This application is a 35 U.S.C. §371 national stage application of International Patent Application PCT/EP2006/063255 (published as WO 2006/134153), filed Jun. 15, 2006, which claimed priority of European Patent Application 05109085.0, filed Sep. 30, 2005; this application further claims priority under 35 U.S.C. §119 of U.S. Provisional Application 60/691,167, filed Jun. 16, 2005.

BACKGROUND OF THE INVENTION

1. Field of the Invention

The present invention relates generally to treatment of diseases and conditions where patients self administer medications. In particular, the invention relates to devices and methods that make the experience of self-administering a medication simpler and/or more enjoyable. The present invention also relates to methods of administering medication and methods of marketing devices and medications to patients. It is particularly well-suited for use by patients who must self inject medications, but is by no means limited to injection devices.

2. Background Art

Many diseases, such as diabetes and growth disorders, typically require a patient to self-administer medications. In many cases, the medications cannot be orally administered. Typically, these medications are self-injected, although new administration routes are being developed; most notably, pulmonary delivery of insulin is being vigorously pursued. While devices for self-injection or inhalation of medication exist, the device typically does not incorporate user friendly feedback. While some infusion pumps include some alarm systems, the typical discrete dosing apparatuses, e.g., an injection pen, does not provide much in the way of auditory feedback to the user. Usually, such injection pens only comprises a very simple mechanical click mechanism which provides a clicking noise for each increment being set on the injection pen

SUMMARY OF THE INVENTION

The present invention improves a patient's experience in self administering a medication. In one embodiment, a medication delivery device, such as an injection pen, is provided with a speaker or other output device that delivers audible, visual and/or tactile feedback to a patient. For example, in one embodiment a chime is emitted from the device when a user first touches the device, when the user changes a setting, or when medication has been successfully delivered from the device.

While the present invention can be incorporated into electromechanically driven medication delivery devices, it can also be incorporated into less complex devices that rely upon purely mechanical components to deliver medication. In some embodiments, the emitted sound can be user selected from a plurality of sounds or it can be downloaded into the device from an external source or from a computer network, such as the Internet.

In one embodiment, the present invention is embodied as a medication delivery device such as an injection pen. The pen is fitted with one or more sensors that sense when the user has initiated use of the pen or even mere contact with the pen. The sensors may sense a variety of actions being taken by the user. These include picking up the pen, removing a cap, attaching a needle, dialing a dose, inserting an injection needle into the user's skin, injecting a dose, removing the needle from the user's skin, replacing the cap, etc. The device may include a sound chip or other electronic or mechanical mechanism for generating sounds. The device may also include an interface for allowing sound patterns to be downloaded to the device.

In one embodiment, various sound patterns are preloaded into the device. The sound patterns may be selected based upon the intended users of the device. For example, in a pen marketed to children the sounds might imitate voices of popular children's cartoons or from other areas of popular children's culture. Thus, this aspect of the present invention is one of the many ways that the present invention is useful in marketing a device and/or the medication contained therein to a particular segment of a population of patients.

In another embodiment, the present invention can provide a way to educate users about the proper operation of the device. For example, when the present invention is incorporated into a pen device, the user can be instructed about the proper operation of the pen via voice synthesized instructions. Even when a patient is fully trained to use a particular device, the present invention is useful in providing the patient with reminders, such as for example, keeping the needle under the skin for a predetermined amount of time after an injection, altering the user that their medication supply is running low, or reminding the user that the medication is about to expire.

BRIEF DESCRIPTION OF THE DRAWINGS

FIG. 1 shows an exemplary embodiment of the present invention in injection pen form.

DETAILED DESCRIPTION OF THE INVENTION

In one exemplary embodiment, the present invention may be incorporated into a standard injection pen, such as an insulin pen. Such pens are described in U.S. Pat. Nos. 6,277,098, 6,302,855, 6,248,090, 6,004,297, 6,235,004, 5,626,566, the contents of which are hereby incorporated by reference.

As is shown in FIG. 1, a pen 1, having a needle 60, with a mechanical dose setting mechanism 11 and mechanical drive mechanism 33 for expelling medicine from the pen can be adapted to include a processor 10, a speaker 20 that is connected to the processor, and user inputs 30, 40. The user inputs can be used to control volume or other functions, such as for example, an on/off switch.

The pen can also include various sensors, such as a touch sensor 50 that responds when a user touches the pen. The touch sensor 50 can be any sensor that reacts when it is touched by a user, such as a pressure sensor, an impedance change sensor, electrical resistance sensing system or any other apparatus that can detect when it is touched. In addition, the pen 1 can include a plurality of other sensors for detecting movement of various parts. For example, the pen 1 can include a cap removal sensor 70 that senses when the cap 100 is removed.

In addition, other sensors can be incorporated into the dose setting mechanism and can be activated by setting a dose. These sensors can be moving contacts or magnetic or any other type of sensor that sense movement of the dose setting mechanism. In addition, the pen 1 can include a needle insertion sensor 200 coupled with the needle so that when the needle is inserted into a skin surface, it is activated. In general, the sensors are interfaced with the processor 10, so that when a sensor is activated a signal is sent to the processor. The processor 10 is configured to generate a sound or is interfaced, coupled, or otherwise cooperates with a sound generating device, such as a sound cart, to generate a sound signal that can drive the speaker 20.

In one embodiment, all sound signals sent to the speaker are the same. In another embodiment, the sound signal varies as a result of different sensors being activated. For example, removing the cap 100 results in one type of sound being generated, turning the dose setting mechanism, results in a distinct sound, and inserting the needle into the skin results in yet another sound.

If the pen 1, contains a needle insertion sensor 200 the processor can be programmed to alert the user via an audible cue when to remove the needle from the skin. This time can be programmed to correspond to the requisite amount of time a needle needs to remain in the skin after an injection (e.g., 10 seconds, usually 4-8 seconds).

In some embodiments, the delivery device that incorporates the present invention might also include a visual display or a tactile display. Accordingly, the processor can display a menu of options available to the user and the user can select the options via the user inputs 30.

Some embodiments may also include an input 300 that allows a user to download chimes, musics etc. to the pen 1. The input can be configured to allow for a wired download or the input can accept wireless communication with an external device, such as a person computer or an network such as the Internet.

In some embodiments, the sound or patient feedback system can be used to provide reminders to a patient. For example, the device can be configured to make sounds or send other audio or visual or tactile reminders to a patient that the device has not been used for a period of time. For example, the device can send a chime if it has not been used in the morning. Other reminders, such as the fact that a normal daily dosage has not been delivered can trigger a sound as well. Multiple sounds can be used for different reminders. Thus, the present invention can be used to improve patient compliance and thus improved patient treatment and outcome.

EXAMPLE 1

A pen according to FIG. 1 can be constructed. In addition the following can be incorporated into such a pen. The pen is preloaded with music from a popular children's movie about fictional toys that come to life. The hero of the movie is a space toy that makes distinctive sounds. In particular, the hero has a built in laser that makes a specific sound when it is fired and has a unique motto that he utters when he is going on an adventure.

In this example, upon removal of the cap from the pen, the pen makes a sound similar to that of the hero's laser when fired. When the user dials a dose, another sound familiar to those who have viewed the movie is created. When the user sticks the needle into a skin surface yet another sound is emitted from the pen. The sound might reassure the user that the painful part is over or that the user was "very brave" or some other words or sounds of encouragement. When sufficient time has elapsed and the needle is to be removed, the pen emits the motto of the hero toy.

EXAMPLE 2

In accordance with example 1, a television commercial can be created showing the use of a pen by a child. The television commercial can then be displayed during, before, or after a presentation of the movie that provided the sounds that are used in the pen. Since the target audience for the movie is children, the commercial will also target the same children. Assuming that the audience of children is large enough, one can calculate the number of potential children in need of such a pen would be watching the commercial. Thus, the present invention can provide a method of using children's television or movie viewing to introduce children and their parents to new medicine delivery technologies that can assist those in need of such technologies.

I claim:

1. A talking manual injection syringe for injecting a dose of medication into a patient, the syringe comprising:
   a speaker;
   a needle;
   a sound generating apparatus connected to the speaker for generating sounds which are comprised of voice instructions that explain the proper operation of the syringe to the patient;
   a cap covering an injection end of the syringe;
   a first sensor that senses when the cap is removed;
   a second sensor for indicating when another operation is performed by the patient with the syringe;
   wherein when the first sensor senses the cap is removed, the sound generating apparatus generates a first sound comprised of a first set of voice instructions indicative of the proper operation of the syringe;
   wherein the second sensor senses when an injection is being administered;
   wherein in response to the injection being administered the sound generator generates a second sound indicative of an injection occurring;
   wherein after the medication is ejected, the sound generator generates a third sound comprised of a second set of voice instructions indicating when it is appropriate to remove the syringe from the patient; and
   wherein the sound generator generates a fourth sound comprised of a third set of voice instructions that notifies the patient that medication supply needs to be refilled.

2. The syringe of claim 1, wherein the syringe comprises multiple sensors.

3. A talking syringe that plays a plurality of voice instructions that instruct a user about the proper way to use the syringe to inject medication from the syringe through a needle,
   the syringe comprising one or more sensors and a speaker structured to broadcast sounds,
   wherein the broadcasted sounds are comprised of voice instructions,
   wherein a first sound is broadcast when a cap covering an injection end of the syringe is removed, the first sound comprising voice instructions that instruct the user about the proper operation of the syringe,
   structure to detect when an injection is being administered, and when an injection is being administered the syringe broadcasts a second sound indicative of an injection occurring, wherein the syringe further broadcasts a third sound comprised of voice instructions that indicate when it is appropriate to remove the syringe from a skin site after an injection, and wherein the syringe broadcasts a fourth sound that is comprised of voice instructions that alerts the user that the medication supply needs to be refilled.

4. A talking syringe comprised of a cap covering an injection end of the syringe, a needle that pierces a patient's skin, a sensor that senses when a cap is removed, a sound generator, and a speaker, wherein the sound generator generates a plurality of sounds that are broadcast on the speaker, wherein the sounds comprise:

a first set of voice instructions about the proper operation of the syringe;

sounds indicative of an injection occurring;

a second set of voice instructions about when it the needle can be removed from the skin of the patient; and a third set of voice instructions providing reminders to refill the medication;

wherein when the sensor senses that the cap covering an injection end of the syringe is removed, the syringe broadcasts the first voice instruction.

5. The talking syringe of claim 4, wherein the sound indicative of an injection occurring is broadcasted during an injection, wherein the second set of voice instructions is broadcast after the sound indicative of the injection occurring is broadcasted and when it is appropriate to remove the needle from the skin, and wherein the third set of voice instructions is broadcasted when the syringe is low on medication.

6. The talking syringe of claim 5, wherein the syringe determines when it is appropriate to remove the needle from the skin by calculating the time required for the needle to remain in the skin after medication ejection.

* * * * *